(12) United States Patent
Klimovitch et al.

(10) Patent No.: US 8,864,757 B2
(45) Date of Patent: Oct. 21, 2014

(54) SYSTEM AND METHOD FOR MEASURING FORCE AND TORQUE APPLIED TO A CATHETER ELECTRODE TIP

(75) Inventors: Gleb V. Klimovitch, Santa Clara, CA (US); John W. Sliwa, Los Altos Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 626 days.

(21) Appl. No.: 12/347,607

(22) Filed: Dec. 31, 2008

(65) Prior Publication Data

US 2010/0168620 A1 Jul. 1, 2010

(51) Int. Cl.

| | |
|---|---|
| A61B 18/18 | (2006.01) |
| A61B 18/04 | (2006.01) |
| A61B 17/42 | (2006.01) |
| A61B 17/46 | (2006.01) |
| A61D 1/10 | (2006.01) |
| A61B 8/00 | (2006.01) |
| A61B 5/04 | (2006.01) |
| A61B 18/14 | (2006.01) |
| A61B 5/00 | (2006.01) |
| A61B 5/042 | (2006.01) |
| A61B 18/02 | (2006.01) |
| A61B 19/00 | (2006.01) |
| A61N 7/02 | (2006.01) |
| A61B 18/24 | (2006.01) |

(52) U.S. Cl.
CPC .............. *A61B 5/042* (2013.01); *A61B 18/02* (2013.01); *A61B 2019/465* (2013.01); *A61B 18/1492* (2013.01); *A61N 7/022* (2013.01); *A61B 18/24* (2013.01); *A61B 5/6885* (2013.01)

USPC ................ 606/37; 606/39; 606/40; 606/41; 606/45; 606/49; 606/20; 606/27; 606/119; 606/10; 600/437; 600/509

(58) Field of Classification Search
USPC ......................................... 600/587
See application file for complete search history.

(56) References Cited

U.S. PATENT DOCUMENTS

| | | | | |
|---|---|---|---|---|
| 3,911,902 | A | * | 10/1975 | Delpy ........................ 600/488 |
| 7,591,816 | B2 | | 9/2009 | Wang et al. |
| 7,815,635 | B2 | | 10/2010 | Wittkampf et al. |
| 7,857,810 | B2 | | 12/2010 | Wang et al. |
| 7,914,528 | B2 | * | 3/2011 | Wang et al. .................. 606/41 |
| 2007/0142749 | A1 | * | 6/2007 | Khatib et al. ................ 600/587 |
| 2008/0161796 | A1 | * | 7/2008 | Cao et al. ...................... 606/41 |
| 2008/0275428 | A1 | | 11/2008 | Tegg et al. |

(Continued)

*Primary Examiner* — Brian Szmal
*Assistant Examiner* — H. Q. Nguyen
(74) *Attorney, Agent, or Firm* — Dykema Gossett PLLC

(57) ABSTRACT

A contact sensing assembly including a catheter including an electrode having a base portion mounted adjacent a head portion of the catheter body. A sensor is disposed adjacent the base portion for measuring compression or tensile forces applied to an electrode tip portion, and includes a predetermined sensitivity. The base and head portions include predetermined rigidity so that forces applied to the electrode tip portion are determinable as a function of the sensitivity and a sensor output. A contact sensing assembly also includes an electrode pipe operatively connected to the catheter body for movement and bending with the catheter body, and an electrode wire disposed in the electrode pipe and including insulation. A change in capacitance resulting from movement of the electrode wire toward the electrode pipe or contact of the electrode wire with the electrode pipe during bending of the catheter correlates to a force applied to the catheter.

3 Claims, 5 Drawing Sheets

(56) References Cited

U.S. PATENT DOCUMENTS

| | | |
|---|---|---|
| 2009/0062642 A1* | 3/2009 | Hauck ........................ 600/429 |
| 2009/0076476 A1* | 3/2009 | Barbagli et al. ............ 604/500 |
| 2009/0247942 A1 | 10/2009 | Kirschenman |
| 2009/0247943 A1 | 10/2009 | Kirschenman et al. |
| 2009/0247944 A1 | 10/2009 | Kirschenman et al. |
| 2009/0247993 A1 | 10/2009 | Kirschenman et al. |
| 2010/0073150 A1 | 3/2010 | Olson et al. |

\* cited by examiner

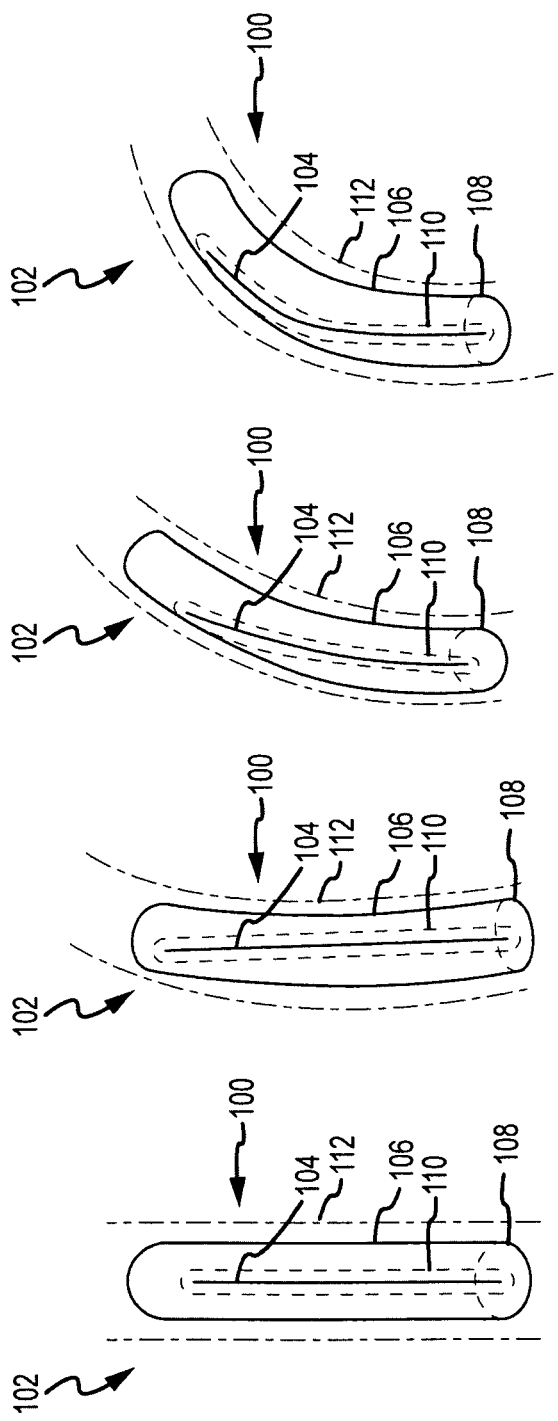

SYSTEM AND METHOD FOR MEASURING FORCE AND TORQUE APPLIED TO A CATHETER ELECTRODE TIP

BACKGROUND OF THE INVENTION a. Field of the Invention

This invention relates to a system and method for assessing the force and torque between an electrode and tissue in a body. In particular, the instant invention relates to a system and method for assessing the force and torque between an electrode tip on a diagnostic and/or therapeutic medical device such as a mapping or ablation catheter and tissue, such as cardiac tissue. The instant invention also relates to a method for sensing and calculating contact force exerted by another component on a tissue, and generally, a method for sensing and calculating contact force on an elongate member when in contact with another component or structure, for medical or non-medical purposes.

b. Background Art

Electrodes are used on a variety of diagnostic and/or therapeutic medical devices. For example, electrodes may be used on cardiac mapping catheters to generate an image of the internal geometry of a heart and electrical potentials within the tissue. Electrodes are also used on ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

The safety and effectiveness of many of diagnostic and/or therapeutic devices is often determined in part by the proximity of the device and the electrodes to the target tissue. In mapping catheters, the distance between the electrodes and the target tissue affects the strength of the electrical signal and the identity of the mapping location. The safety and effectiveness of ablation lesions is determined in part by the proximity of the ablation electrode to target tissue and the effective application of energy to that tissue. If the electrode is too far from the tissue or has insufficient contact with the tissue, the lesions created may not be effective. On the other hand, if the catheter tip containing the electrode contacts the tissue with excessive force, the catheter tip may perforate or otherwise damage the tissue (e.g., by overheating). Therefore, to successfully ablate live tissue, the electrode should be applied to the tissue with proper force. When ablating and moving an electrode, in addition to the magnitude of the force, knowledge of direction of the force (i.e. multi-axial measurement) and further the torque acting on the electrode tip are important for estimating the distribution of pressure and stress over an electrode tip surface.

Contact force between a catheter electrode and tissue has typically been determined using one or more of the following methods: clinician sense, fluoroscopic imaging, intracardiac echo (ICE), atrial electrograms (typically bipolar D-2), pacing thresholds, evaluation of lesion size at necropsy and measurement of temperature change at the energy delivery site. Each of these methods has disadvantages, however.

For example, although a clinician can evaluate contact force based on tactile feedback from the catheter and prior experience, the determination depends largely on the experience of the clinician and is also subject to change based on variations in the mechanical properties of catheters used by the clinician. The determination is particularly difficult when using catheters that are relatively long (such as those used to enter the left atrium of the heart).

Because fluoroscopic images are two-dimensional projections and blood and myocardium attenuate x-rays similarly, it can be difficult to quantify the degree of contact force and detect when the catheter tip is not in contact with the tissue.

Intracardiac echo can be time consuming and it can be difficult to align the echo beam with the ablation catheter. Further, intracardiac echo does not always permit the clinician to confidently assess the degree of contact and can generate unacceptable levels of false positives and false negatives in assessing whether the electrode is in contact with tissue.

Atrial electrograms do not always correlate well to tissue contact and are also prone to false negatives and positives. Pacing thresholds also do not always correlate well with tissue contact and pacing thresholds can be time-consuming and also prone to false positives and negatives because tissue excitability may vary in hearts with arrhythmia. Evaluating lesion size at necropsy is seldom available in human subjects, provides limited information (few data points) and, further, it is often difficult to evaluate the depth and volume of lesions in the left and right atria. Finally, temperature measurements provide limited information (few data points) and can be difficult to evaluate in the case of irrigated catheters.

The inventors herein have thus recognized a need for a system and method for determining the contact force and torque upon an electrode tip, both during RF ablation and when driving the RF electrode to the ablation site, that will minimize and/or eliminate one or more of the above-identified deficiencies.

BRIEF SUMMARY OF THE INVENTION

It is desirable to provide a system and method for determining the degree of coupling between an electrode and a tissue in a body. In particular, it is desirable to be able to determine a degree of electrical coupling between electrodes on a diagnostic and/or therapeutic medical device such as a mapping or ablation catheter and tissue, such as cardiac tissue.

A system for assessing a degree of coupling between an electrode and a tissue in a body in accordance with one embodiment of the invention may include a contact sensing assembly including a catheter having a body having a proximal end and a distal end, and an electrode including a tip portion and a base portion mounted adjacent a head portion of the catheter body. One or more force and torque sensors may be disposed generally adjacent the base portion and may include one or more pressure sensors for measuring pressure applied to the electrode tip portion and providing a pressure signal related to the measured pressure, with the pressure sensor including a predetermined sensitivity. The base and head portions may include a predetermined rigidity so that force applied to the electrode tip portion may be determinable as a function of the predetermined sensitivity and the pressure signal.

For the assembly described above, in an embodiment, the assembly may include a plurality of pressure sensors, and the individual pressure sensor output signals allow a vector reconstruction of a net tip contact force using a vector addition algorithm or relationship. In an embodiment, the assembly may further include a plurality of pressure sensors, and the force applied to the electrode tip portion may be determinable as a sum of a voltage output signal of each pressure sensor respectively divided by the predetermined sensitivity of each pressure sensor. In an embodiment, the assembly may further include a plurality of pressure sensors, and torque applied to the electrode tip portion may be determinable as a function of a voltage output signal of each pressure sensor respectively divided by the predetermined sensitivity of each pressure sensor, and a distance of the pressure sensors from a central axis of the electrode.

For the assembly described above, in an embodiment, the assembly may include three symmetrically disposed pressure sensors, and for an electrode having a central axis disposed along a z-direction, torque applied to the electrode tip portion may be determinable as follows: $T\_y = \frac{3}{4} \cdot D \cdot (V\_c/\alpha\_c - V\_a/\alpha\_a - V\_b/\alpha\_b)$, where $T\_y$ may be the torque applied to the electrode tip portion in a y-direction, D may be a diameter of a circle passing through the centers of each pressure sensor, V may be a voltage output of each respective pressure sensor, and a may be the predetermined sensitivity of each respective pressure sensor. In an embodiment, the assembly may include three symmetrically disposed pressure sensors, and for an electrode having a central axis disposed along a z-direction, torque applied to the electrode tip portion may be determinable as follows: $T\_x = \sqrt{3}/2 \cdot D \cdot (V\_a/\alpha\_a - V\_b/\alpha\_b)$, where $T\_x$ may be the torque applied to the electrode tip portion in a x-direction, D may be a diameter of a circle passing through the centers of each pressure sensor, V may be a voltage output of each respective pressure sensor, and $\alpha$ may be the predetermined sensitivity of each respective pressure sensor.

For the assembly described above, in an embodiment, the generally distal end of the catheter may include a coupling member connecting the electrode to the catheter body. In an embodiment, the coupling member may include an elastic material. In an embodiment, the pressure sensors may be emplaced in an interface between two or more annular or circular rings. In an embodiment, the tip portion of the electrode may include an irrigation port. The electrode may include an RF ablation electrode, a HIFU ablation transducer, a laser ablation assembly, a cryogenic ablation assembly, an ultrasonic imaging apparatus, an electrical cardiac pacing electrode, or an electrical cardiac sensing electrode. The pressure sensors may be fabricated using flex circuit technology, lithographic technology, thin-film technology, and/or thick film technology. In an embodiment, the assembly may further include a proximal control handle including one or more catheter deflection or articulation controls, and one or more switches for controlling a diagnostic or therapeutic function of the electrode. The force applied to the electrode tip may be utilized for automatically limiting a maximum force, warning of a high or unacceptable force, giving visual or audible feedback to a practitioner regarding a tissue contact force, warning of a loss of contact force or contact, and/or warning of a contact force which may be too low.

In an embodiment, a system for assessing a degree of coupling between an electrode and a tissue in a body may include a contact sensing assembly including a catheter including a body having a proximal end and a distal end, and an electrode including a tip portion and a base portion mounted adjacent a head portion of the catheter body. One or more sensors may be disposed generally adjacent the base portion for measuring compression or tensile forces applied to the electrode tip portion and providing an output signal related to the measured forces, with the sensor including a predetermined sensitivity. The base and head portions may include a predetermined rigidity so that the compression or tensile forces applied to the electrode tip portion are determinable as a function of the predetermined sensitivity and the output signal.

For the assembly described above, in an embodiment, the assembly may include a plurality of sensors, and the individual sensors each generate an output signal that together provide a vector reconstruction of a net tip contact force using a vector addition algorithm or relationship. In an embodiment, the assembly may include a plurality of sensors, and the compression or tensile forces applied to the electrode tip portion may be determinable as a sum of the output signals of each sensor respectively divided by the predetermined sensitivity of each sensor. In an embodiment, the assembly may include a plurality of sensors, and torque applied to the electrode tip portion may be determinable as a function of the output signal of each sensor respectively divided by the predetermined sensitivity of each sensor, and a distance of the sensors from a central axis of the electrode.

For the assembly described above, in an embodiment, the assembly may include three symmetrically disposed sensors, and for an electrode having a central axis disposed along a z-direction, torque applied to the electrode tip portion may be determinable as follows: $T\_y = \frac{3}{4} \cdot D \cdot (V\_c/\alpha\_c - V\_a/\alpha\_a - V\_b/\alpha\_b)$, where $T\_y$ may be the torque applied to the electrode tip portion in a y-direction, D may be a diameter of a circle passing through the centers of each sensor, V may be a voltage output of each respective sensor, and $\alpha$ may be the predetermined sensitivity of each respective sensor. In an embodiment, the assembly may include three symmetrically disposed sensors, and for an electrode having a central axis disposed along a z-direction, torque applied to the electrode tip portion may be determinable as follows: $T\_x = \sqrt{3}/2 \cdot D \cdot (V\_a/\alpha\_a - V\_b/\alpha\_b)$, where $T\_x$ may be the torque applied to the electrode tip portion in a x-direction, D may be a diameter of a circle passing through the centers of each sensor, V may be a voltage output of each respective sensor, and $\alpha$ may be the predetermined sensitivity of each respective sensor.

For the assembly described above, in an embodiment, the generally distal end of the catheter may include a coupling member connecting the electrode to the catheter body. In an embodiment, the coupling member includes an elastic material. In an embodiment, the sensors may be emplaced in an interface between two or more annular or circular rings. In an embodiment, the tip portion of the electrode may include an irrigation port. The electrode may include an RF ablation electrode, a HIFU ablation transducer, a laser ablation apparatus, a cryogenic ablation assembly, an ultrasonic imaging transducer, a cardiac pacing electrode, or a cardiac sensing electrode. The sensors may be fabricated using flex circuit technology, lithographic technology, thin-film technology, and/or thick film technology. In an embodiment, the assembly may include a proximal control handle including one or more catheter deflection or articulation controls, and one or more switches for controlling a diagnostic or therapeutic function of the electrode. The compression or tensile force applied to the electrode tip may be utilized for automatically limiting a maximum force, warning of a high or unacceptable force, giving visual or audible feedback to a practitioner regarding a tissue contact force, warning of a loss of contact force or contact, and/or warning of a contact force which may be too low. The sensor may be a resistive force sensor, a capacitive force sensor, or an optical force sensor.

In an embodiment, a system for assessing a degree of coupling between an electrode and a tissue in a body may include a contact sensing assembly including a catheter having a body having a proximal end and a distal end, an electrode pipe disposed in the catheter body, and an electrode wire disposed in the electrode pipe and including insulation thereon. A change in capacitance resulting from movement of the electrode wire toward the electrode pipe or contact of the electrode wire with the electrode pipe during bending of the catheter may directly correlate to a force applied to the catheter.

For the assembly described above, in an embodiment, the electrode wire and electrode pipe may be mechanically coupled toward a distal end thereof. An electrode operatively connected to the catheter may include an RF ablation electrode, a HIFU ablation transducer, a laser ablation apparatus, a cryogenic ablation assembly, an ultrasonic imaging transducer, a cardiac pacing electrode, or a cardiac sensing electrode. In an embodiment, the assembly may further include a proximal control handle including one or more catheter deflection or articulation controls, and one or more switches for controlling a diagnostic or therapeutic function of an electrode operatively connected to the catheter. The compression or tensile force applied to the electrode tip may be utilized for automatically limiting a maximum force, warning of a high or unacceptable force, giving visual or audible feedback to a practitioner regarding a tissue contact force, warning of a loss of contact force or contact, and/or warning of a contact force which may be too low.

In an embodiment, a system for assessing a degree of coupling between an electrode and a tissue in a body may include a contact sensing assembly including a catheter having a body having a proximal end and a distal end, an electrode pipe operatively connected to the catheter body for movement and/or bending with the catheter body, and an electrode wire disposed in the electrode pipe and including insulation thereon. A change in capacitance resulting from movement of the electrode wire toward the electrode pipe or contact of the electrode wire with the electrode pipe during bending of the catheter may directly correlate to a force applied to the catheter.

The foregoing and other aspects, features, details, utilities and advantages of the invention will be apparent from reading the following description and claims, and from reviewing the accompanying drawings.

BRIEF DESCRIPTION OF THE DRAWINGS

FIGS. 5a-5d are partial isometric diagrammatic views of a catheter structure in accordance with another embodiment of the invention.

DETAILED DESCRIPTION OF EMBODIMENTS OF THE INVENTION

Figure 1:
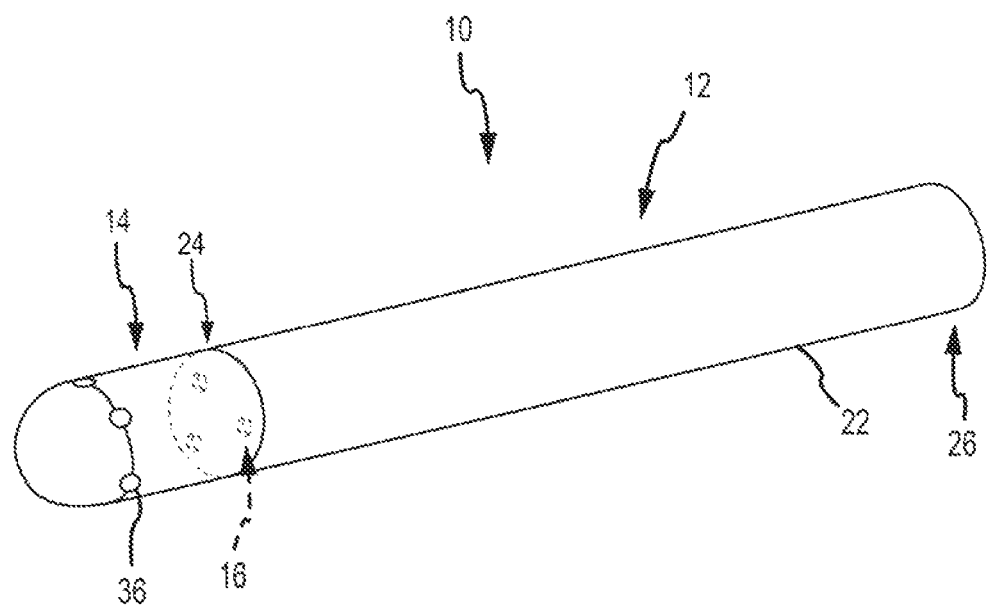
FIG. 1 is a partial perspective view of a catheter assembly in accordance with an embodiment of the invention.

Referring now to the drawings wherein like reference numerals are used to identify like components in the various views, FIG. 1 illustrates an exemplary embodiment of a contact sensing assembly 10 as provided by the invention. In a general form, referring to FIGS. 1 and 2, contact sensing assembly 10 may include a catheter 12, an electrode 14 connected to the catheter, and a force and torque sensor 16 for interacting with base 18 of electrode 14 or alternatively with head 20 of catheter body 22 if sensor 16 is mounted on base 18. In another embodiment, contact sensing assembly 10 may include a first interactive component and a second interactive component. The contact sensing assembly may be used in the diagnosis, visualization, and/or treatment of tissue (such as endocardial tissue) in a body. Contact sensing assembly 10 may be used in a number of diagnostic and therapeutic applications, such as for example, the recording of electrograms in the heart, the performance of cardiac ablation procedures, and/or various other applications. The catheter assembly can be used in connection with a number of applications that involve humans, or other mammals, for tissue observation, treatment, repair or other procedures. Moreover, the invention is not limited to one particular application, but rather may be employed by those of ordinary skill in the art in any number of diagnostic and therapeutic applications, and for medical or non-medical purposes. For example, the contact sensing assemblies disclosed herein may be usable in combination with a robotic catheter system (e.g. disclosed in commonly owned and co-pending applications titled "Robotic Catheter Manipulator Assembly" (U.S. patent application Ser. No. 12/347,826, filed Dec. 31, 2008, now U.S. Pat. No. 8,317,744, issued Nov. 27, 2012); "Robotic Catheter Device Cartridge" (U.S. patent application Ser. No. 12/347,835, filed Dec. 31, 2008, published Oct. 1, 2009 under U.S. Publication No. 2009/0247943); "Robotic Catheter Rotatable Device Cartridge" (U.S. patent application Ser. No. 12/347,842, filed Dec. 31, 2008, now U.S. Pat. No. 8,317,745. issued on Nov. 27, 2012); and "Robotic Catheter System with Dynamic Response " (U.S. Patent Application No. 61/142,008, tiled Dec. 31, 2008), the respective disclosures of which are incorporated herein by reference in their entirety), for example, for coupling to a computer controlled catheter or surgical instrument for real-time feedback and precise control during a procedure.

Referring to FIGS. 1-4, catheter 12 of the invention may include body 22 having a distal end 24 and a proximal end 26. Body 22 of catheter 12 is generally tubular in shape, although other configurations of the catheter may be used as known in the industry. If desired, the outer portion of catheter 12 may have a braided outer covering therein providing increased torqueability and strength. The catheters of the invention vary in length and are attached to a handle or other type of control member that allows a surgeon or operator of the catheter to manipulate the relative position of the catheter within the body from a remote location, as recognized by one of ordinary skill in the art.

An embodiment of a system and method for measuring force and torque applied to the tip of electrode 14, namely contact sensing assembly 10, will now be described in detail.

Figures 2, 3:
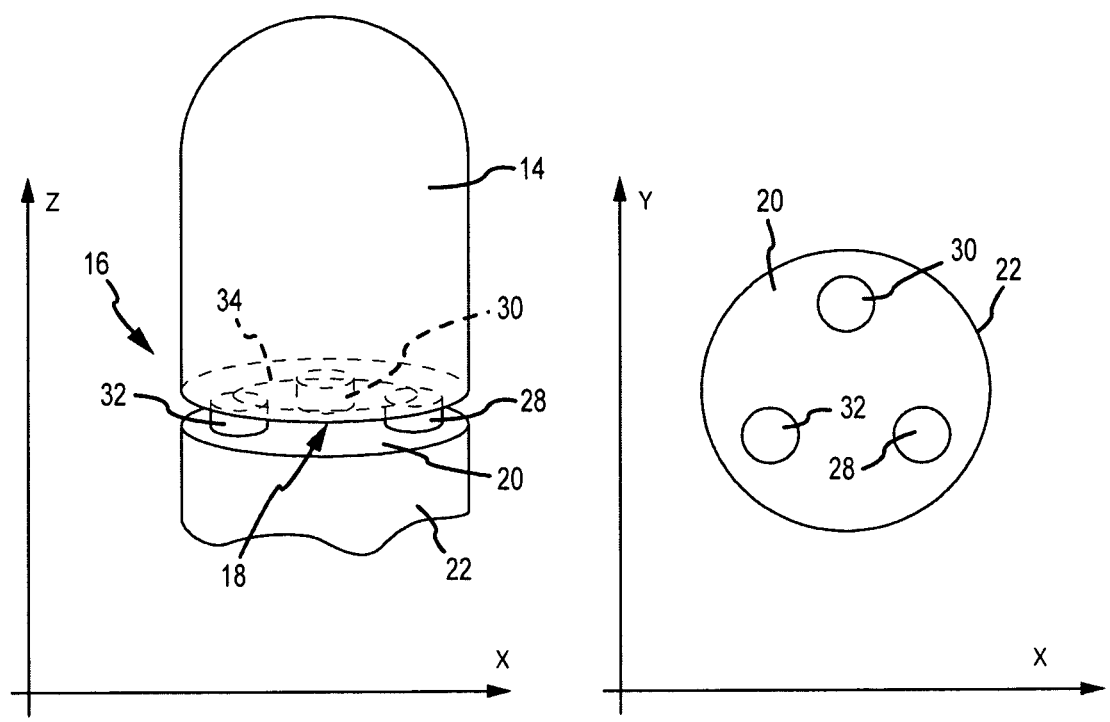
FIG. 2 is an isometric diagrammatic view of an electrode area according to the invention, illustrating exemplary force and torque sensors.
FIG. 3 is a top view of the electrode area of FIG. 2, with the electrode removed for clarity.

As shown in FIG. 3, body 22 of catheter 12 may generally include sensors 28, 30, 32 of force and torque sensor 16 mounted on head 20 in a tri-axial arrangement. Alternatively, sensors 28, 30, 32 may he generally located between a "neck" area of electrode 14 and a support portion on the body. The body of electrode 14, particularly near base 18 and the area of body 22 adjacent head 20, may be sufficiently rigid to permit any forces (axial or transverse) applied to electrode 14 to be measured by force and torque sensor 16. The sensor arrangement of FIGS. 2 and 3 may specifically measure force along the electrode axis $F_z$, and two components of torque in a plane perpendicular to the electrode axis, namely $T_x$ and $T_y$. If needed, the force in the x and y directions may be determined from the torque components.

The method of calculating force and torque from sensors 28, 30, 32 will now be described in detail.

Without loss of generality, all three sensors 28, 30, 32 may be presumed to have the same sensitivity "α" (α is the proportionality constant between force applied to a sensor and the sensor's electrical output, and represents as predetermined value for each sensor). Given forces in the z-direction applied to each sensor F_a, F_b, F_c (e.g. forces applied to sensors 28, 30, 32), the sensor outputs will be V_a=α F_a, V_b=αF_b, V_c=α F_c, respectively. It should be noted that the term "forces in the z-direction" does not imply force and torque sensor 16 only measures forces in the z-direction. Namely, if a force is applied in the y-direction in FIG. 3, while sensors 28, 32 may measure as negative (e.g. tensile) force, sensor 30 would measure a positive (e.g. compression) force, with force and torque sensor 16 determining the force in the z-direction based on the respective measurements at each sensor 28, 30, 32.

The force/torque components may be given by the following equations:

$$F\_z=(V\_a+V\_b+V\_c)/\alpha,$$

$$T\_y=\mathrm{sqrt}(3)/(2*\alpha)*D*(V\_c-V\_a/2-V\_b/2), \text{ and}$$

$$T\_x=\mathrm{sqrt}(3)/(2*\alpha)*D*(V\_a-V\_b), \text{ where "D" is the diameter of circle 34 in the x-y plane passing through the centers of sensors 28, 30, 32.}$$

If each sensor 28, 30, 32 has a different sensitivity α (e.g. α_a, α_b, α_c), then the sensor outputs would be:

$$V\_a=\alpha\_a F\_a, V\_b=\alpha\_b F\_b, V\_c=\alpha\_c F\_c.$$

The force and torque components may be given by the following equations:

$$F\_z=V\_a/\alpha\_a+V\_b/\alpha\_b+V\_c/\alpha\_c,$$

$$T\_y=\tfrac{3}{4}*D*(V\_c/\alpha\_c-V\_a/\alpha\_a-V\_b/\alpha\_b), \text{ and}$$

$$T\_x=\mathrm{sqrt}(3)/2*D*(V\_a/\alpha\_a-V\_b/\alpha\_b)$$

Thus the sensor arrangement of FIGS. 2 and 3 may specifically measure force along the electrode axis $F_z$, and two components of torque in the plane perpendicular to the electrode axis, namely $T_x$ and $T_y$, with the force and torque being determined as discussed above.

Figure 4:
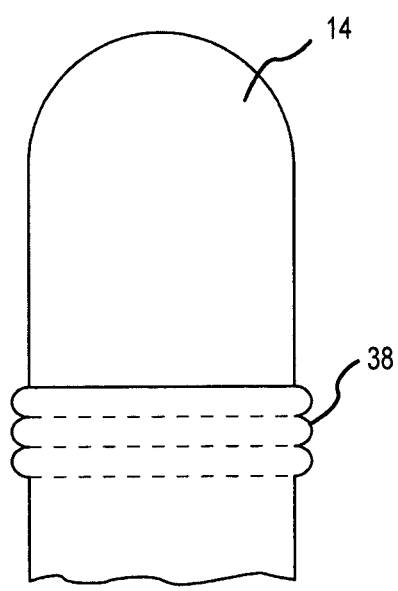
FIG. 4 is a partial diagrammatic view of a catheter assembly in accordance with another embodiment of the invention.

Referring to FIG. 4, electrode 14 and body 22 may optionally be connected by an elastic hermetic neck, with elastic hermetic neck 38 further allowing only predetermined relative movement of electrode 14 and body 22, and thus force and torque determination by sensors 28, 30, 32. It should be noted that while neck 38 is illustrated as including ridges, neck 38 may optionally be a smooth structure, or another elastic coupling, element such as those disclosed in commonly owned and co-pending application titled "Optic-Based Contact Sensing Assembly and System" (U.S. patent application Ser. No. 11/941,073, filed Nov. 15, 2007, published Nov. 6, 2008 under U.S. Publication No. 2008/0275428).

Thus by measuring the z-directional forces applied to each sensor 28, 30, 32, force and torque sensor 16 provides feedback on the amount of force of electrode 14 onto a tissue (e.g. $F_z$), as well as the torque applied to electrode 14 (e.g. $T_x$ and $T_y$).

Referring next to FIGS. 5a-5d, another embodiment of a system and method for measuring force applied to the tip of an electrode, namely contact sensing assembly 100, will be described in detail.

Generally, contact sensing assembly 100 of FIGS. 5a-5d may estimate the lateral (xy) force of a tip electrode (e.g. electrode 14) onto tissue (e.g. heart or other tissue) from the bending curvature of a catheter 102 near the tip of an electrode. Such a sensor of curvature may be either resistive or capacitive. If capacitive, an inner electrode wire 104 (made for example of stainless steel) may he disposed inside a coaxial outer electrode pipe 106, with wire 104 and electrode pipe 106 being mechanically connected at bottom area 108. Outer electrode pipe 106 may be made of a flexible plastic, with the interior surface thereof covered with a thin metal film (e.g. gold). Electrode wire 104 may he covered with a thin layer of insulation 110 made of, for example, Teflon®, to prevent shorts, and may also include insulation at the mechanical coupling at bottom area 108. Outer electrode pipe 106 may be mechanically coupled to catheter body 112 so that they both bend similarly.

In operation, as shown in FIG. 5c, when electrode pipe 106 bends together with catheter body 112, the capacitance between electrode wire 104 and electrode pipe 106 increases as electrode wire 104 (which has insulation thereon) begins to move toward electrode pipe 106. As shown in FIG. 5d, as electrode pipe 106 bends more together with catheter body 112, the contact area between electrode wire 104 and electrode pipe 106 increases, to thus further increase the capacitance between electrode wire 104 and electrode pipe 106. The increase in capacitance is measured and correlated to the amount of force on the tip of the electrode (e.g. electrode 14 based on the degree of bending of catheter body 112. For example, for a catheter body having a predetermined flexibility based on the application of a predetermined force, the capacitance may be directly correlated to the amount of force being applied to catheter body 112. Likewise, for any given catheter body having a predetermined flexibility based on the application of a predetermined force, a capacitance factor may be provided to determine the amount of force being applied to the catheter body based on measured capacitance.

As discussed above, contact sensing assembly 100 may be either resistive or capacitive. For an assembly 100 based on changes in resistivity, a resistive solution may he injected inside electrode pipe 106 and anti-short standoffs (not shown) may be used instead of insulation 110. The resistive solution, such as saline, may be used to fill assembly 100 right before or during surgery.

Thus by measuring the change in capacitance or resistivity between inner electrode wire 104 and outer electrode pipe 106, contact sensing assembly 100 provides feedback on the amount of force of an electrode (e.g. electrode 14) onto tissue.

Those skilled in the art would appreciate in view of this disclosure that various modifications may be made to the aforementioned force and torque sensors without departing from the scope of the invention.

For example, for force and torque sensor 16, more components of force and torque may be measured by using more sensors 28, 30, 32. Sensors 28, 30, 32 may be positioned differently than the arrangement of FIGS. 2 and 3 (e.g. asymmetrically relative to the central axis of the electrode), or the sensors may be positioned so that their axes of sensitivity are not parallel to the electrode central axis.

Further, electrode 14 may also be configured to include a means for irrigating. For example, without limitation, as shown in FIG. 1, the incorporation of at least one irrigation port 36 within electrode 14 may provide an irrigated electrode tip. An irrigated electrode tip allows for the cooling of electrode 14, for instance, through the transporting of fluid through electrode 14 and around the surface of the tissue. A number of different types of electrodes, irrigated and non-irrigated, may he connected and incorporated for use of an electrode 14 according to embodiments of the invention depending on the type of procedures being done. Such irrigated electrodes include, but are not limited to, those disclosed in U.S. patent application Ser. No. 11/434,220 (filed May 16, 2006), now U.S. Pat. No. 7,857,810, issued Dec. 28, 2010; Ser. No. 10/595,608 (filed Apr. 5, 2007), now U.S. Pat. No. 7,815,635, issued Oct. 19, 2010; Ser. No. 11/646,270 (filed Dec. 28, 2006), now U.S. Pat. No. 7,591,816, issued Sep. 22, 2009; Ser. No. 11/647,346 (filed Dec. 29, 2006), now U.S. Pat. No. 7.914,528, issued Mar. 29, 2011; and 60/828, 955 (filed Oct. 10, 2006), each of which is hereby incorporated by reference as though fully set forth herein.

Figure 6A:
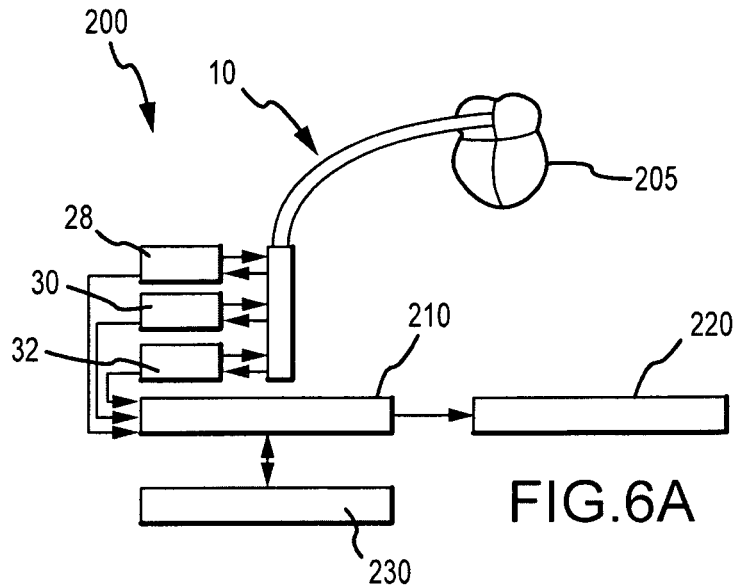
FIGS. 6a-6f are schematic overviews of a system for measuring force and torque in accordance with alternate embodiments of the invention.
Figure 6B:
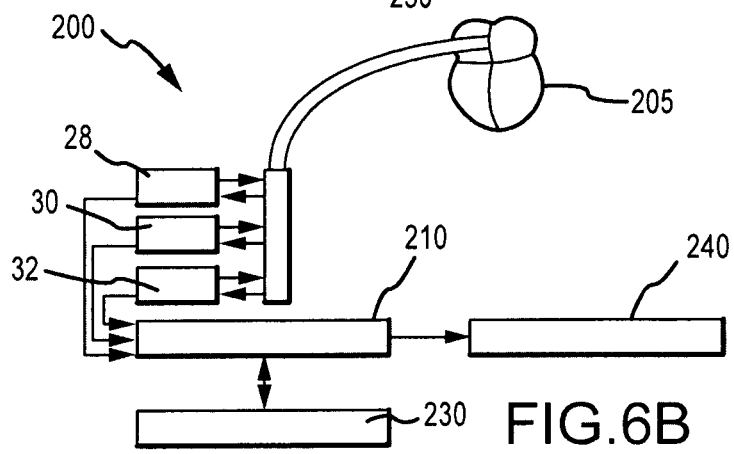
Figure 6C:
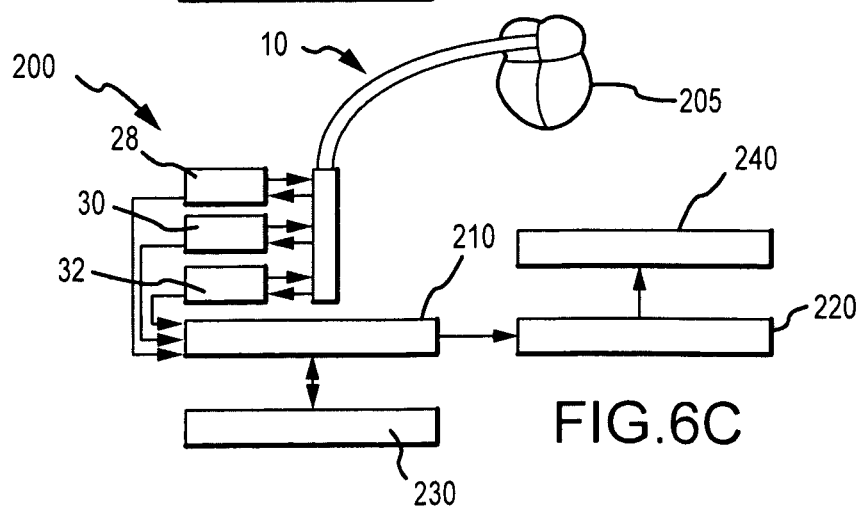
Figure 6D:
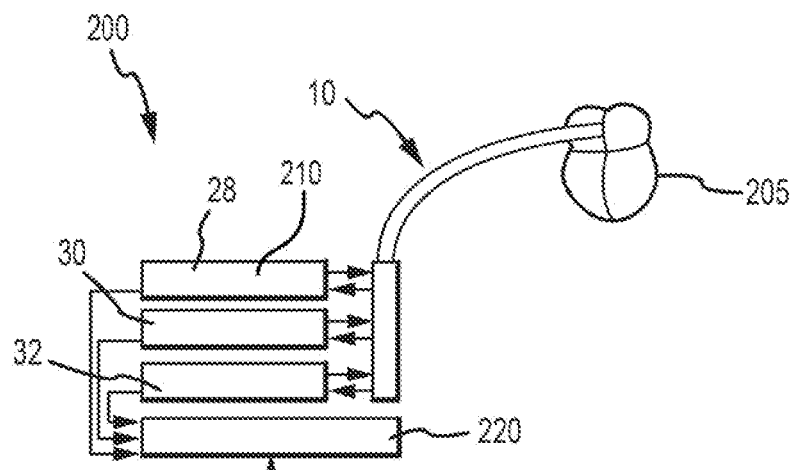
Figure 6E:
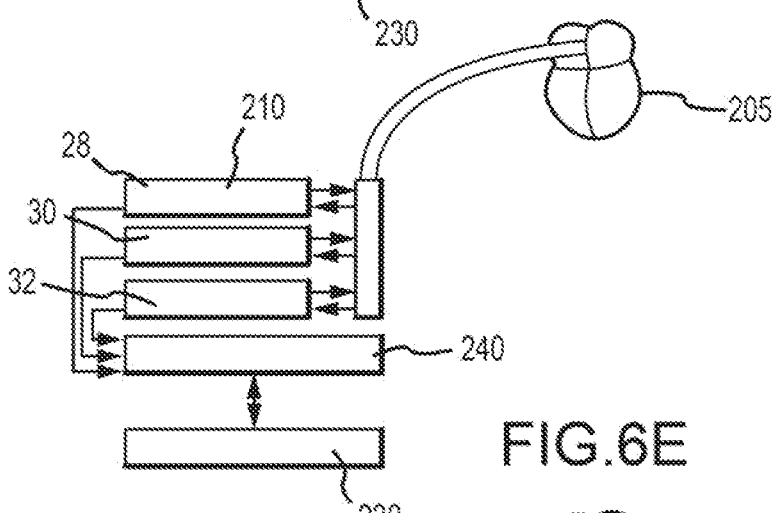
Figure 6F:
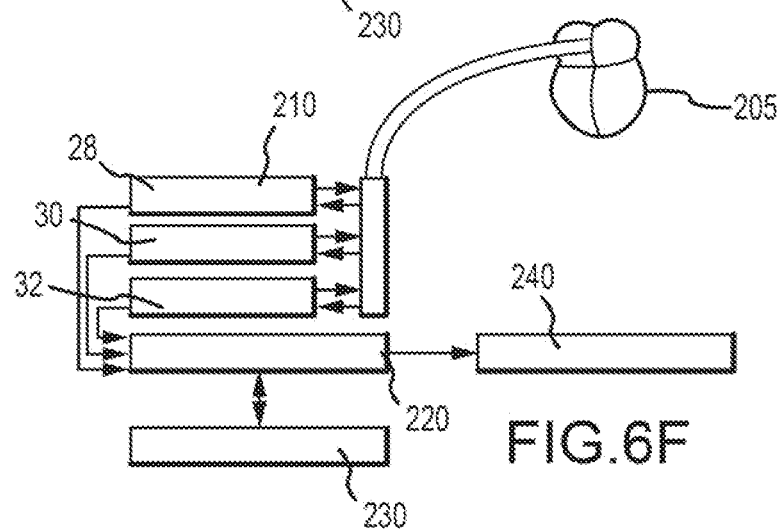

The invention further discloses a force-based catheter system 200, as shown in FIGS. 6A-6F, that includes assemblies 10 or 100 (note: only assembly 10 illustrated) of the invention connected to a signal converter 210 (such as an analog to digital converter) and an operator interface 220, which may further include a computer and display, for processing the force signals received from assemblies 10 or 100 in connection with positioning and contact with tissue, such as myocardial tissue 205. This force-based information is processed to determine the contact force exerted on electrode 14 or the electrode for assembly 100. A calibration system 230 (i.e., calibration software) may be further provided to readily correlate the pressure or capacitance measurements to the external force or torque on the electrode. A mapping system 240, such as the EnSite®NavX®System, may be integrated with system 200 to provide a visualization and mapping system for use in connection with assemblies 10 or 100 of the invention. In an alternate embodiment, as shown in FIGS. 6D-6F, signal converter 210 may be integrated with assemblies 10, 100, such that the force or torque signal is directly processed and provided on operator interface 220. Overall, each of these components may be modified and/or integrated with one another depending on the design of the force/torque system as recognized by one of ordinary skill in the art.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A contact sensing assembly comprising:
   a catheter including a body having a proximal end and a distal end;
   a bendable electrode pipe comprising an inner surface, a proximal end, and a distal end; wherein the electrode pipe is completely enclosed in the catheter body; and
   a flexible electrode wire including insulation thereon and comprising a proximal end and a distal end, wherein the electrode wire is completely enclosed in the electrode pipe and setoff from the inner surface of the electrode pipe when the catheter body is in a non-bent configuration, wherein the proximal end of the electrode wire is mechanically coupled to the proximal end of the electrode pipe; and wherein a non-coupled portion of the electrode wire is adapted to move toward and away from the inner surface of the electrode pipe when the catheter body bends,
   wherein a change in capacitance resulting from a change in a relative distance between the non-coupled portion of the electrode wire and the inner surface of the electrode pipe during bending of the electrode pipe directly correlates to a force applied to the catheter.

2. The assembly according to claim 1, wherein an electrode operatively connected to the catheter comprises one of an RF ablation electrode, a HIFU ablation transducer, a laser ablation apparatus, a cryogenic ablation assembly, an ultrasonic imaging transducer, a cardiac pacing electrode, and a cardiac sensing electrode.

3. The assembly according to claim 1, wherein the force applied to the catheter is utilized for at least one of:
   a) automatically limiting a maximum force;
   b) warning of a high or unacceptable force;
   c) giving visual or audible feedback to a practitioner regarding a tissue contact force;
   d) warning of a loss of contact force or contact; and
   e) warning of a contact force which is too low.

* * * * *